United States Patent [19]

Anello et al.

[11] 4,326,068

[45] Apr. 20, 1982

[54] PROCESS OF PREPARING HEXAFLUOROTHIOACETONE DIMER

[75] Inventors: Louis G. Anello, Hamburg; Michael Van Der Puy, Cheektowaga, both of N.Y.

[73] Assignee: Allied Corporation, Morris Township, Morris County, N.J.

[21] Appl. No.: 216,035

[22] Filed: Dec. 15, 1980

[51] Int. Cl.³ .......................................... C07D 339/00
[52] U.S. Cl. ...................................................... 549/89
[58] Field of Search ........................................... 549/89

[56] References Cited

PUBLICATIONS

Dyatkin et al., Tetrahedron, vol. 29 (1973), pp. 2759–2767.

*Primary Examiner*—Richard Raymond
*Attorney, Agent, or Firm*—Thomas D. Hoffman

[57] ABSTRACT

An improved process for the reaction of hexafluoropropene with elemental sulfur and alkali metal fluoride such as KF, in an aprotic solvent selected from the group consisting of acetonitrile dimethylacetamide, dimethylformamide, dimethyl sulfoxide and N-methyl pyrrolidone under substantially one atmosphere pressure and at tempertures of between about 25° and 100° C. is disclosed. The preferred alkali metal fluoride is KF and the preferred aprotic solvent is dimethylformamide.

11 Claims, No Drawings

PROCESS OF PREPARING HEXAFLUOROTHIOACETONE DIMER

BACKGROUND OF THE INVENTION

This invention relates to an improved process for preparing hexafluorothioacetone dimer by reacting hexafluoropropene with an alkali metal fluoride and sulfur in a selected aprotic solvent and specifically to the use of an aprotic solvent comprising acetonitrile, dimethylacetamide, dimethylformamide, dimethyl sulfoxide or N-methyl pyrrolidone.

The preparation of hexafluorothioacetone dimer by reaction of hexafluoropropene with sulfur and alakli metal fluoride such as KF in tetramethylene sulfone or nitrobenzene at a temperature of 120° to 150° C. in an autoclave under elevated pressures is disclosed by B. L. Dyatkin et al., in *Proceedings of the Academy of Sciences of the USSR*, 183, 1018–1021 (1968), and by B. L. Dyatkin et al. in *Tetrahedron*, 29, 2759–2767 (1973). However, the use of elevated pressures and high temperatures requires special equipment. Since both references report production of other products such as oligomers of hexafluoropropene and compounds containing the perfluoroisopropylthio group, the process becomes involved with increased separation steps and expense, and the overall yield of hexafluorothioacetone dimer is lowered.

Another method for preparing hexafluorothioacetone dimer by reaction of hexafluoropropene with sulfur over an activated carbon catalyst at 425° C. is disclosed by K. V. Martin, *J. Chem. Soc.*, 2944 to 2947 (1964). However, the high temperatures required makes the process economically unattractive.

Hexafluorothioacetone dimer [2,2,4,4-tetrakis(trifluoromethyl)-1,3-dithiethane] is an intermediate in the production of hexafluoroisobutylene, and of hexafluoroacetone which is useful as an insecticide and for the preparation of high molecular weight polymers.

In the course of development of the process of the present invention, it was discovered that the reaction of equimolar proportions of hexafluoropropene and sulfur in the presence of potassium fluoride and tetramethylene sulfone at atmospheric pressure conditions did not result in formation of hexafluorothioacetone dimer.

Accordingly, it is an object of the present invention to provide a process for the preparation of hexafluorothioacetone dimer by reaction of hexafluoropropene with sulfur and alkali metal fluoride in a suitable solvent at atmospheric pressure conditions.

This and other objects and advantages of the present invention will be apparent from the description which follows.

SUMMARY OF THE INVENTION

The present invention provides an improved process for preparing hexafluorothioacetone dimer wherein hexafluoropropene is contacted with elemental sulfur and alkali metal fluoride in a solvent. The improvement comprises using an aprotic solvent comprising a member selected from the group consisting of acetonitrile, dimethylacetamide, dimethylformamide, dimethyl sulfoxide and N-methyl pyrrolidone.

There is further provided a process for preparing hexafluorothioacetone dimer which comprises reacting, at a temperature between about 25° and about 100° C. and under substantially one atmosphere of pressure, hexafluoropropene with elemental sulfur and anhydrous alkali metal fluoride in a substantially anhydrous aprotic solvent consisting essentially of a member selected from the group consisting of acetonitrile, dimethylacetamide, dimethylformamide, dimethyl sulfoxide and N-methyl pyrrolidone, wherein the molar ratio of hexafluoropropene:elemental sulfur:said alkali metal fluoride is between about 1:1:0.06 and about 1:3:5.

DETAILED DESCRIPTION OF THE INVENTION AND OF PREFERRED EMBODIMENTS

The present invention, in its broadest aspect, utilizes a solvent comprising an aprotic solvent selected from the group consisting of acetonitrile, dimethylacetamide, dimethylformamide, dimethyl sulfoxide and N-methyl pyrrolidone, to allow the contact of hexafluoropropene with elemental sulfur and alkali metal fluoride to proceed, under the surprisingly mild reaction conditions of substantially one atmosphere of pressure and at temperatures between about 25° and 100° C., to give hexafluorothioacetone dimer in high yield and high conversion, i.e. at least about 60% to more than about 90% of said dimer based on the weight of hexafluoropropene. In a preferred embodiment, the present invention employs a solvent which comprises at least 50% by volume of an aprotic solvent selected from the group consisting of acetonitrile, dimethylacetamide, dimethylformamide, dimethyl sulfoxide and N-methyl pyrrolidone. The selected solvent of the present invention may conveniently contain no more than 50% by volume of a diluent or other solvent such as tetramethylene sulfone, which does not interfere with the process of the present invention. In a more preferred embodiment, the solvent consists essentially of one of the selected aprotic solvents selected from the group consisting of acetonitrile, dimethylacetamide, dimethylformamide, dimethyl sulfoxide and N-methyl pyrrolidone. Dimethylformamide is the preferred solvent in each aspect of the present invention.

It was surprising to discover that the reaction of gaseous hexafluoropropene with elemental sulfur and alkali metal fluoride in a solvent would proceed with high yield under such mild conditions in view of the report by the Russian workers that elevated pressures and high temperatures (120° to 150° C.) were used for reaction of hexafluoropropene with elemental sulfur and KF in tetramethylene sulfone to produce hexafluorothioacetone dimer (See *Tetrahedron*, 29, 2759 (1973), and the finding by Applicants that no hexafluorothioacetone dimer was isolated when hexafluoropropene was contacted with elemental sulfur and KF in tetramethylene sulfone at atmospheric pressure and at temperatures of 45° to 65° C.

In accordance with the broadest aspect of the present invention, a mixture is formed by mixing elemental sulfur with an alkali metal fluoride, preferably anhydrous alkali metal fluoride, in a solvent comprising at least 50% by volume of one of said selected aprotic solvents such as dimethylformamide, more preferably consisting essentially of a selected aprotic solvent such as dimethylformamide, and perfluoropropene, is bubbled subsurface to the mixture for a time sufficient to produce hexafluorothioacetone dimer. After the reaction is completed, the hexafluorothioacetone dimer is recovered by phase separation or fractional distillation.

Temperatures of between about 25° and about 100° C. are adequate for the conversion to hexafluorothioacetone dimer to take place. Reaction temperatures of between about 40° and 70° C. are preferred for high yields, i.e. above about 90% of hexafluorothioacetone dimer.

The present invention proceeds under substantially one atmosphere of pressure (absolute); no external pressure is applied. Special equipment such as autoclaves and high pressures are not required. This is particularly surprising for the reaction of a gas with sulfur and alkali metal fluoride in the selected aprotic solvents described hereinabove.

The alkali metal fluorides found useful in the present invention are NaF, LiF, KF and CsF. Solely for economic reasons, KF is preferred. It is reported that alkali metal fluorides catalyze the reaction of sulfur with perfluoroalkenes (See C. G. Krespan et al., *Fluorine Chemistry Reviews*, 1, 145 (1967). Anhydrous alkali metal fluoride is preferred. Anhydrous KF is more preferred.

The molar ratio of hexafluoropropene:elemental sulfur:alkali metal fluoride for the present invention is between about 1:1:0.06 and about 1:3:5. While the preferred molar ratio of hexafluoropropene:elemental sulfur:alkali metal fluoride is about 1:1:0.06 with the preferred dimethylformamide, higher molar ratios of 1:3:5 can conveniently be used without effecting conversion and yields of hexafluorothioacetone dimer. The hexafluorothioacetone dimer formed when the solvent consists essentially of dimethylformamide is substantially free of other compounds containing sulfur and perfluorinated three-carbon moieties, such as $[(CF_3)_2CF-S]_2$ or $(CF_3)_2CF-S-C(F)=CCF_3(CF_2)_2CF_3$. By the term "substantially free of other compound", it is meant that the desired dimer contains no more than about 2% by weight of dimer of other impurities. (See Example V).

In a preferred aspect of the present invention the total reaction mixture is substantially anhydrous, i.e., no more than about 0.05% water by weight. The alkali metal fluoride is conveniently made essentially anhydrous by vacuum drying. The selected aprotic solvent is treated with an appropriate drying agent to produce an aprotic solvent having no more than about 0.05% water, usually about 0.02% water by weight.

For the case of dimethylformamide having no more than about 0.05% water by weight, the reaction of hexafluoropropene with elemental sulfur and anhydrous KF is run for a time sufficient to produce hexafluorothioacetone dimer which is conveniently separated from the reaction mixture by crystallization. The dimethylformamide recovered contains anhydrous KF and as such is recycled for further reaction between additional hexafluoropropene and elemental sulfur. This special recycling feature is only available in view of the present invention because of the mild reaction conditions employed which allow production of high purity hexafluorothioacetone dimer substantially free of the side products such as $[(CF_3)_2CFS]_2$.

The following examples are intended to illustrate, but not to limit, the present invention compared to the broader scope set forth in the claims which follow.

EXAMPLE I

Preparation of Hexafluorothioacetone Dimer (HFTA Dimer)

Into a 500 mL 3-neck flask equipped with a thermometer, mechanical stirrer, gas inlet tube and a water cooled condenser was charged 20 g (0.625 mole) sulfur, 22 g (0.38 mole) anhydrous KF, 125 mL dimethylformamide and 125 mL tetramethylene sulfone. The mixture was heated to 40° C. and hexafluoropropylene was bubbled subsurface to the reaction mixture. After 5 hours, there was added an additional 30 g (0.94 mole) of sulfur to the mixture. Temperature was allowed to rise to 60°–65° C. After 10 hours reaction time, 326 g (2.16 mole) hexafluoropropene was charged and 73 g (0.485 mole) recovered unreacted. Total reacted was 253 g (1.70 moles) of hexafluoropropene. Sulfur reacted was 52 g (1.32 moles). The lower phase, 301 g, of the two phase reaction mixture (647.5 g) was distilled on the spinning band column to give a forefraction, 38 g, bp 75°–93° C.; an intermediate fraction, 21 g, bp 93°–105° C.; a major fraction 200 g, bp 105°–110° C., and a residue 30 g, bp >110° C. The composition of the fractions indicated the presence of 225 g (0.62 mole) hexafluorothioacetone dimer, $[(CF_3)_2C-S]_2$, for a 73% yield based on hexafluoropropene reacted. The IR spectrum of the recovered hexafluorothioacetone dimer was consistent with the expected structure.

EXAMPLE II

Into a 500 mL 3-neck flask equipped as above was charged with 48 g (1.50 mols) sulfur, 87.0 g (1.50 moles) of anhydrous potassium fluoride and 200 mL dimethylformamide. The mixture was heated to 40°–45° C. and 218 g (1.45 moles) hexafluoropropene added during 2¼ hours. An additional 16 g (0.50 mole) sulfur was added and 88 g (0.58 mole) of hexafluoropropene added during a 2 hour period at 55° C. Total sulfur reacted was 64 g (2.0 moles) and total hexafluoropropene added was 306 g (2.04 moles). The contents of the flask were poured into a separatory funnel and the lower layer, 352.5 g, was phase separated from the upper layer. The lower layer was chilled to −10° C. and dimethylformamide solvent separated from the crystallized hexafluorothioacetone dimer. The recovered dimer was fractionally distilled to give 285 g (0.78 mole) of dimer for a 76% conversion and yield.

The recovered upper layer consisting of mainly dimethylformamide and anhydrous KF was recharged back to the reaction flask along with 40 mL make-up solvent and 48 g (1.50 moles) of sulfur. Hexafluoropropene (244 g, 1.63 moles) was passed into the reaction mixture over a 2½ hour period at 50°–65° C. and the separation process repeated. There was recovered 278 g (0.765 mole) of hexafluorothioacetone dimer after distillation of the crude product for a 94% conversion and yield.

The reaction was continued for a third cycle. Forty mL of make-up solvent and 48 g (1.50 moles) of sulfur were charged to the reaction flask containing recovered dimethylformamide and KF. Hexafluoropropene (259 g, 1.73 moles) was passed into the reaction mixture for a period of 2 hours at 65° C. and the separation process repeated. There was recovered 292 g (0.80 mole) of hexafluorothioacetone dimer for a 92% conversion and yield.

Comparative Example III

Attempted Preparation of Hexafluorothioacetone Dimer

Into a 500 mL flask as described in Example II was charged 32 g (1.0 mole) sulfur, 22 g (0.38 mole) of anhydrous KF and 200 mL tetramethylene sulfone. The mixture was heated to 45°–65° C. and 60 g (0.40 mole) of hexafluoropropene was fed to the reaction mixture over a 3 hour period. There was recovered 60 g (0.40 mole)

of unreacted hexafluoropropene in the dry-ice-acetone trap indicating that no reaction with sulfur had taken place. No hexafluorothioacetone dimer was isolated from the reaction mixture.

EXAMPLE IV

Preparation of Hexafluorothioacetone Dimer

Into a 500 mL flask as described in Example II was charged 48 g (1.50 mole) of sulfur, 5 g (0.086 mole) anh. KF and 200 mL of dimethyl sulfoxide. Hexafluoropropene (133 g, 0.89 mole) was reacted over a 6 hour period at 55° C. to give 104 g (0.275 mole) of crude hexafluorothioacetone dimer for a 62% conversion and yield.

EXAMPLE V

A mixture of 200 mL dry dimethylformamide, 23 g (0.72 mole) sulfur and 5.0 g KF in the apparatus of Example II were heated to 40° C. and hexafluoropropene was bubbled in at a rate of about 1 g/min. The temperature rose to 52°–57° C. After 96 g (0.64 mole) hexafluoropropene had been added, an additional 23 g sulfur was charged. Hexafluoropropene was added until a total of 199.5 g (1.33 mole) was used (2.3 h). The whole mixture was cooled to −20° C. and filtered. The solid was washed with cold dimethylformamide. After allowing the solid to melt, it was filtered (to remove sulfur and KF), phase separated, and washed twice with 50 mL water. This gave 199.7 g pale yellow hexafluorothioacetone dimer product (82.5% yield) of 98% purity by GC.

Comparative Example VI

To 200 mL dry $CH_3CN$ in the apparatus of Example II were added 2.0 CsF and 11.1 g (0.347 mole) sulfur. After warming to 40° C., hexafluoropropene (57.2 g) was bubbled in over 1.67 h, but 11.4 g was recovered in a cold trap so that 45.8 g (0.305 mole) hexafluoropropene had reacted. During the reaction time, the maximum temperature was 59° C. At the end of the hexafluoropropene addition, the mixture was cooled to room temperature and filtered. The filtrate was diluted with 250 mL $H_2O$ and filtered again. The crude product (lower layer) was washed with water to give 38.0 g product which was 44% hexafluorothioacetone dimer by GC.

Comparative Example VII

Into the 500 mL 3-neck flask as described in Example II was charged 16 g (0.50 moles) sulfur, 5.0 g anhydrous KF and 200 mL of anhydrous acetone. Hexafluoropropene (32 g, 0.23 moles) was bubbled in subsurface to the liquid reaction mixture over a 5 hour period; the temperature was 22° to 35° C. There was recovered 20 g (0.143 moles) of unreacted hexafluoropropene in the dry-ice-acetone trap indicating that essentially no reaction with sulfur had taken place. No hexafluorothioacetone was isolated.

We claim:

1. In a process of preparing hexafluorothioacetone dimer wherein hexafluoropropene is contacted with elemental sulfur and alkali metal fluoride in a solvent, the improvement which comprises using an aprotic solvent comprising a member selected from the group consisting of acetonitrile, dimethylacetamide, dimethylformamide, dimethyl sulfoxide and N-methyl pyrrolidone while maintaining an absolute pressure of the contact at substantially one atmosphere.

2. The process of claim 1 wherein said solvent comprises at least about 50% by volume of a member selected from the group consisting of acetonitrile, dimethylacetamide, dimethylformamide, dimethyl sulfoxide and N-methyl pyrrolidone.

3. The process of claim 1 wherein said solvent consists essentially of a member selected from the group consisting of acetonitrile, dimethylacetamide, dimethylformamide, dimethyl sulfoxide and N-methyl pyrrolidone.

4. The process of claim 1, 2 or 3 wherein the contact temperature is between about 25° C. and about 100° C.

5. The process of claim 4 wherein the contact temperature is between about 40° and 70° C.

6. The process of claim 4 wherein the contact temperature is between about 40° and 70° C. and the aprotic solvent is dimethylformamide.

7. The process of claim 6 wherein the alkali metal fluoride is KF.

8. A process for preparing hexafluorothioacetone dimer which comprises reacting, at a temperature between about 25° and about 100° C. and under substantially one atmosphere of pressure, hexafluoropropene with elemental sulfur and anhydrous alkali metal fluoride in a substantially anhydrous aprotic solvent consisting essentially of a member selected from the group consisting of acetonitrile, dimethylacetamide, dimethylformamide, dimethyl sulfoxide and N-methyl pyrrolidone, wherein the molar ratio of hexafluoropropene:elemental sulfur:said alkali metal fluoride is between about 1:1:0.06 and about 1:3:5.

9. The process of claim 8 wherein the anhydrous alkali metal fluoride is anhydrous KF and said aprotic solvent is dimethylformamide and wherein said molar ratio is about 1:1:0.06.

10. The process of claim 9 which further comprises separating hexafluorothioacetone dimer from a mixture comprising anhydrous KF and said dimethylformamide, recovering said hexafluorothioacetone and recycling said mixture to the contacting step of the process.

11. The process of claim 8 wherein the hexafluorothioacetone dimer is substantially free of other compounds containing sulfur and perfluorinated three-carbon moiety.

* * * * *